United States Patent [19]

Altman et al.

[11] Patent Number: 4,929,335

[45] Date of Patent: May 29, 1990

[54] METHOD FOR CONTROL OF VISBREAKER SEVERITY

[75] Inventors: Lawrence J. Altman; Byung C. Choi, both of Cherry Hill; Grant G. Karsner, Voorhees Township, Camden County, all of N.J.

[73] Assignee: Mobil Oil Corporation, New York, N.Y.

[21] Appl. No.: 386,173

[22] Filed: Jul. 28, 1989

Related U.S. Application Data

[62] Division of Ser. No. 222,858, Jul. 22, 1988, Pat. No. 4,880,748.

[51] Int. Cl.$^5$ ............................................. C10G 9/00
[52] U.S. Cl. ........................... 208/106; 208/DIG. 1; 436/60
[58] Field of Search ................. 208/106, 107, DIG. 1; 436/60

[56] References Cited

U.S. PATENT DOCUMENTS

| | | | |
|---|---|---|---|
| 3,733,476 | 5/1973 | Hopkins et al. | 208/DIG. 1 |
| 3,751,229 | 8/1973 | Bajek et al. | 208/DIG. 1 |
| 3,759,820 | 9/1973 | Boyd | 208/64 |
| 4,615,791 | 10/1986 | Choi et al. | 208/107 |
| 4,673,486 | 6/1987 | Orihashi et al. | 208/106 |
| 4,698,313 | 10/1987 | Stewart | 208/DIG. 1 |
| 4,846,958 | 7/1989 | Feldman et al. | 208/106 |

*Primary Examiner*—Anthony McFarlane
*Attorney, Agent, or Firm*—Alexander J. McKillop; Charles J. Speciale; Malcolm D. Keen

[57] ABSTRACT

A method for assaying incompatible sediment in a blended heavy fuel oil is provided. The method is based on measuring total light absorption at 1600 nanometers wavelength, for example, of two or more samples blended to different viscosities, at least one such sample being at specification viscosity. The method may be used to control visbreaker severity so as to reduce the large ERT safety margin commonly used by refiners.

5 Claims, 1 Drawing Sheet

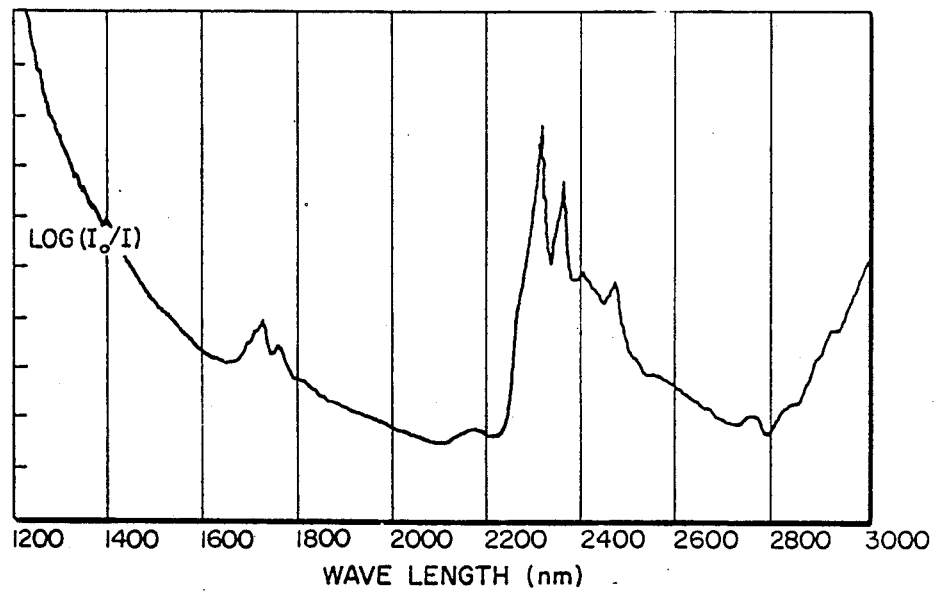
FIG. 1  LIGHT TRANSMISSION SPECTRA
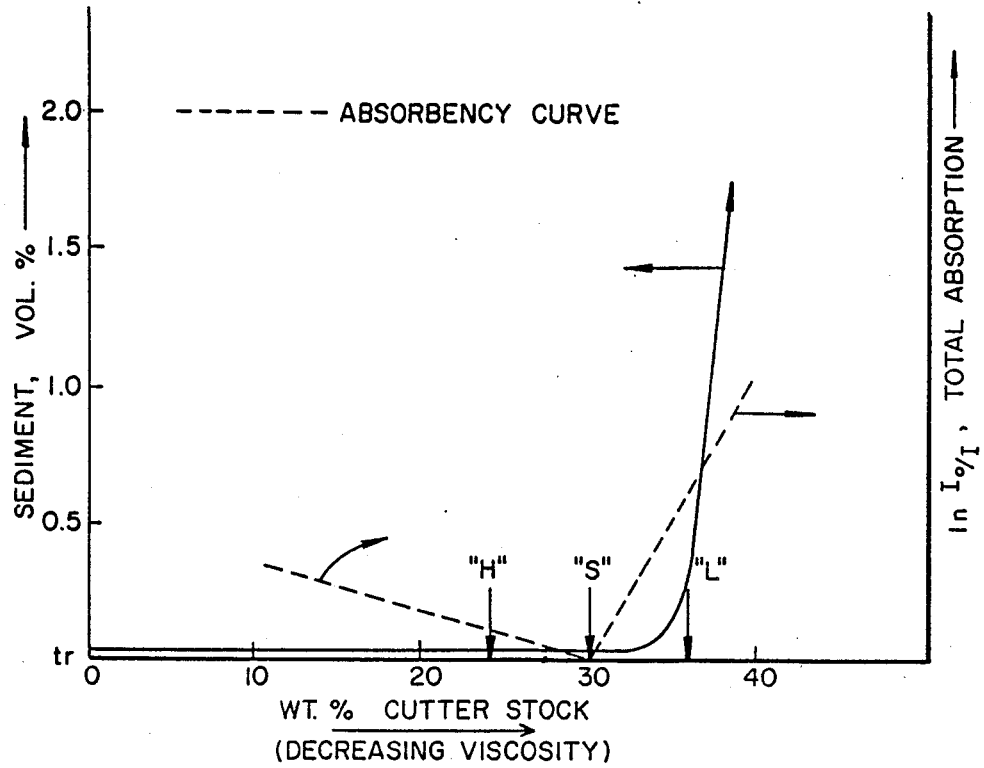
FIG. 2

METHOD FOR CONTROL OF VISBREAKER SEVERITY

This is a divisional of copending application Ser. No. 222,858, filed on July 22, 1988 now U.S. Pat. No. 4,880,748.

FIELD OF THE INVENTION

This invention is concerned with visbreaking. In particular, it is concerned with a rapid optical method for determining the presence of incompatible sediment in a heavy fuel oil blend. The method is adaptable for controlling the operating severity of a visbreaker by on-line monitoring of the sediment-forming tendency of a visbroken oil.

Viscosity reduction (commonly referred to as "visbreaking" is one of the few thermal cracking processes still used in petroleum refining. Its principal purpose is to reduce the quantity of high value distillates a refiner must add to a very viscous atmospheric or vacuum residuum in order to produce a heavy fuel oil (HFO) meeting commercial viscosity specifications.

The visbreaking process is well known and need not be described here in any detail. Typically, a vacuum residuum is heated in a furnace to about 850°–900° F. (typically about 875° F.) and held at this temperature in a soaking coil for a time sufficient to give the desired amount of thermal cracking. The process forms 1–2 percent gas, 5–10 percent naphtha, and 20–30 percent distillate gas oil. Naphtha and lighter fractions are removed completely from the visbroken oil in order to meet the flash point and safety requirements. The gas oil content serves as cutter stock, thereby reducing the requirement for external distillate as cutter stock. (See Kirk Othmer, Encyclopedia of Chemical Technology, 3rd Edition, Vol. 17, page 215 and the references contained therein, incorporated herein by reference for background purposes.)

In general, visbreaking is ideally operated at maximum severity consistent with satisfactory heavy fuel oil compatibility and with tolerable coke laydown in the furnace tubes. In practice, the severity of visbreaking is usually specified in terms of equivalent reaction time (ERT), in seconds, at 800° F. Such specification will be used herein.

The visbreaker charge stock is a complex mixture of hydrocarbons, some of which incorporate heteroatoms. For present purposes, it will be convenient to regard the mixture as containing heavy hydrocarbon oils which are easily thermally cracked, and colloidal asphaltene particles which are nonvolatile and not readily cracked. The hydrocarbon oils in the charge stock function as peptizing agents that normally keep the asphaltenes in colloidal solution. During the course of the visbreaking reaction, heavy hydrocarbon oils are thermally converted to lower boiling compounds, some of which are removed thus concentrating the asphaltenes in the visbroken resid. If the visbreaking reaction proceeds too far, the asphaltenes may precipitate from the oil to form deposits in the cracking furnace and/or form incompatible sediment when the visbroken resid is diluted to specification viscosity with cutter stock. (It is interesting to note that visbreaking by itself does not form sediment, and the stability of excessively visbroken resids can be considerably improved if they are blended with highly aromatic cutter stocks.)

The marketability of a blended HFO is dependent on its being substantially free of incompatible sediment. In the case of such an oil for marine use, for example, excessive sediment can disrupt the operation of the centrifuge commonly used to separate the oil from water before feeding to the engine, and result in consequent shutdown of the engine itself. Specifications for such oil usually include a maximum of 0.3 vol. % of incompatible sediment. Less demanding service, such as for inland use, may tolerate up to about 1.0 vol. % of sediment.

The term "sediment" (sometimes also called sludge) as used herein refers to insoluble organic matter in blended HFO's. For present purposes, the insoluble organic matter may be regarded as arising from the flocculation of colloidally dispersed asphaltenes, and the exclude extraneous matter such as clay, sand or rust. Such extraneous matter, if present, may be determined according to the procedure described by American Society for Testing Materials, in ASTM D 473. It is generally known that the tendency to form sediment of a visbroken resid when diluted to specification viscosity with distillate cutter stock depends on the nature of the resid, the nature of the cutter stock, and especially on the severity of the visbreaking. With increased visbreaking severity, the tendency of the colloidal asphaltenes to agglomerate to sediment on dilution to specification viscosity increases markedly when the severity exceeds a certain level, i.e. the visbroken resid becomes incompatible with the cutter stock at specification viscosity (or, for test purposes, at some other viscosity). In such instances, the HFO is herein designated "incompatible", and the organic sediment contained therein is referred to as "incompatible sediment". It is important to note that different resids visbroken to the same ERT can exhibit very different compatibility behavior.

There is no single, industry-wide test procedure to assay the incompatible sludge in a HFO. Instead, there are two widely used types of assay. One type relies on centrifugation, and is exemplified by method M-1006 in use by Mobil Oil Corporation. Briefly, this method uses a 100 ml representative sample of oil which is placed in a conical centrifuge tube and centrifuged at 150° F. for three hours. The tube is then removed and allowed to drain for about 30 minutes. Sediment volume is read directly and reported as vol %. A second type of test relies on filtration, and is exemplified by a Shell method. Briefly, 10 grams of sample is filtered under pressure at 212° F. through a dried Whatman No. 50 hardened filter paper, following which the residue is washed three times with 10 cc portions of n-heptane. The paper and residue are dried, and the weight of residue determined and reported as wt %. These two methods do not give the same results. However, the results are correlatable. Both of the described methods are capable of assaying "existent" incompatible sediment (on an as-is or as-received sample), and "potential" incompatible sediment, the latter test being made on a sample of HFO blended further to 30 cs (centistokes) that has undergone accelerated aging, e.g., for 24 hours at 100° C. A larger value for potential sediment compared with existent sediment is attributable to further flocculation of asphaltenes during aging. Unless otherwise qualified, the term "incompatible sediment" as used herein refers to existent incompatible sediment.

The sediment-forming tendency of a visbroken resid is of considerable importance to the refiner as well as to marketer and to the user. The refiner must control the visbreaking severity to insure compatibility and efficient visbreaking even when the visbreaker feedstock is drastically changed, thus presenting a moving target; and the marketer and user need to know whether the blended HFO is (or will remain) substantially free of incompatible sludge.

In general, available methods are very time consuming procedures requiring at least several hours for a measurement, and as a consequence are relatively costly. As a result, the methods are inadequate as a tool for controlling visbreaker severity. Long turnaround times for test results force refiners to operate with a large ERT safety margin to ensure an acceptable HFO quality. Most commercial units that visbreak to produce blended HFO operate about 150–250 ERT below the theoretical limit since there is severe economic penalty for producing unstable HFO.

It is an object of this invention to provide a method for rapidly assaying the content of incompatible sediment in a heavy fuel oil prepared by blending a visbroken residuum with one or more cutter stocks.

It is a further object of this invention to provide a method which is insensitive to crude source for rapidly assaying the content of incompatible sediment in a heavy fuel oil.

It is a still further object of this invention to provide a method for on-line control of the operating severity of a visbreaker, whereby insuring compatibility with reduced ERT safety margin.

These and other objects will become apparent on reading this entire specification and the appended claims.

BRIEF DESCRIPTION OF THE DRAWING

FIG. 1. Light Absorbency of Resid, 1200–3000 nm.
FIG. 2. Sediment vs. Visbroken Resid Concentration.

BRIEF SUMMARY OF THE INVENTION

We have now found that the presence of incompatible sediment in a HFO blend is readily assayed by measurement of total absorption of light having a wavelength in the range of 1200–3000 nm using at least two samples that differ only in the concentration of visbroken residuum. Selection of a wavelength where the absorbency of the residuum is low makes the method substantially independent of crude source, and it also increases the sensitivity of the method to the presence of imcompatible sediment. Preferred wavelengths for the absorbency measurements are 1600 and 2080 nm.

The foregoing method is adaptable to on-line control of the visbreaker severity. For visbreaker control purposes, three samples of visbreaker effluent or, as alternatively termed, rundown are diluted with cutter stock to provide a first HFO blend at higher than specification viscosity, a second HFO blend at specification viscosity (referred to herein as the specification blend), and a third HFO blend at lower than specification viscosity. The visbreaker severity is adjusted to force incompatible sediment formation in the third blend without forming incompatible sediment in the specification blend.

DETAILED DESCRIPTION OF THE INVENTION

The method of this invention is based on the discovery that light absorbency of petroleum oils obeys Beer's Law when the HFO samples are free of incompatible sediment. However, a marked increase in absorbency is observed (i.e. a departure from Beer's Law) when incompatible sediment is present. This makes it possible, simply by comparing the amount of light transmitted by two or more samples diluted with different amounts of the same cutter stock, to determine whether or not incompatible sediment is present in a blended HFO sample. The magnitude of the departure is sensitive to wavelength, and best results are obtained at 1600 or 2080 nm (nanometers). Using the selected wavelength also makes it possible to control the severity of a visbreaker.

The concept of this invention is best explained by reference to FIGS. 1 and 2 of the drawing. FIG. 1 illustrates an absorption curve typical for a raw residuum. FIG. 2 represents the generalized behavior of a satisfactory visbroken residuum on dilution with progressively larger amounts of cutter stock. The horizontal branch of the curve corresponds to the dilution range over which substantially no incompatible sediment forms, and the transition and near-vertical branch to the sediment-forming range. The point "S" represents dilution to specification viscosity, e.g. about 30 cs. Similarly, points "H" and "L" represent dilution to higher and lower viscosity, e.g. to 40 and 20 cs, respectively.

To assay a HFO sample for the presence of incompatible sediment, it is necessary only to compare one sample of the HFO with one sample prepared from the same visbroken resid but at a higher concentration of resid. If the slope of the absorbency curve is negative as one progresses from lesser to greater dilution (i.e. from the sample at higher concentration of resid to that at lower concentration), then absence of incompatible sediment at the lower resid concentration is assured. Conversely if the slope is positive, then incompatible sediment is present at the lower resid concentration.

Control of visbreaker severity requires three dilution samples of the visbreaker rundown corresponding to points H, S and L in FIG. 2. If the absorption of sample S is not greater than sample H, but sample L shows significantly higher total absorption, (corresponding with FIG. 2), then no adjustment of visbreaker severity is required. On the other hand, if sample L does not have higher absorption than sample S, this indicates that the visbreaker severity is below optimum (i.e. the visbreaking curve shown in FIG. 2 has shifted to the right) and an increase in severity is called for. By the same token, if sample S contains incompatible sediment, i.e. has higher absorption than sample L, a decrease of severity is required to restore optimum severity. It will be evident to one skilled in the art that the illustration provided above with the specification viscosity being 30 cs and the other two samples being set at 20 cs and 40 cs are only one of a number of possible sets that are operative for control purposes. For example, allowable variability of visbreaker severity can be enlarged or narrowed by making the difference between the specification sample and the low viscosity sample larger or smaller than 10 cs, respectively. While in general the specification sample is preferably maintained at or very close to specification viscosity, a minimum tolerance for excessive dilution can be insured by using as specification sample one at 28 cs, for example. These and other modifications, including the use of four test samples instead of three to more precisely define the ERT margin of safety, will be evident to one skilled in the art, and such variants are within the ambit of this invention.

While the foregoing description has been couched in terms of existent incompatible sediment, this invention is readily modifiable for determining potential incompatible sediment. This is most readily done by heating and maintaining the dilution samples at an elevated temperature in the range of 200° to 750° F. for about 5 to 30 minutes, prior to measuring the total absorbency. Such variants also are within the ambit of the present invention.

While not wishing to be bound by theory, it is believed that the present invention can be explained based on the principles of light absorption and light scattering. When a light beam is passed through a light absorbing/scattering colloidal solution, the amount of light transmitted through the solution is reduced as a result of both absorption and scattering. If the incident-light intensity is $I°$ and the transmitted-light intensity over pathlength L is I, Beer's Law expresses a linear relationship for the absorption, $\theta$ (without scattering) in terms of the concentration of absorbing material, $C_a$, and pathlength, L, as $$\theta = \ln I_o/I = \alpha C_a L \quad (1)$$

where C is the absorption coefficient. Generally, the absorption coefficient is a function of wavelength.

On the other hand, isotropic light scattering, or turbidity T (Tyndall effect), generally follows a theory of Mie/Rayleigh and it can be expressed as $$\tau = \ln I_o/I = k C_s L D^m \quad (2)$$

where k is the scattering coefficient, $C_s$ is the concentration of scattering material and D is the particle size of the scattering material. The scattering coefficient, k, is also a function of wavelength and the refractive index of the solution. The magnitude of exponent m varies from 4 to 6.5 depending on the ratio of particle size to wavelength.

In a dilute resid solution, absorption and scattering take place as independent phenomena. Therefore we formally define the total absorbance $\phi$, as the sum of absorption and scattering and express it as $$\phi = \theta + \tau \quad (3)$$

$$= \alpha C_a L + k C_s L D^m \quad (4)$$

At a given wavelength, Equation (4) indicates that the net absorbance is linear in the concentration of the absorbing and scattering species but highly sensitive to the particle size of the scattering species, since m varies from about 4 to 6.5, as noted above.

We have observed, in the absence of flocculated asphaltenes, that the total absorbency gradually decreases as a visbroken resid is blended with increments of distillate cutter stock. Without wishing to be bound by theory, this can be explained as follows based on the foregoing discussion. A portion of the absorbency of the visbroken resid is attributable to the colloidally dispersed asphaltenes. Progressive dilution with a distillate stock (free of asphaltenes), so long as the diluted samples form compatible blends, reduces the concentration of colloidal asphaltenes and therefore reduces total absorbency. The net effect is to produce a baseline with a gentle negative slope for log $I°/I$ with progressive dilution. This is in contrast with the zero-slope baseline obtained by centrifuge or filtration assay over the substantially incompatible sediment-free range. With formation of incompatible sediment however, the slope of the total absorbance becomes very strongly positive, as it also does with assay by centrifuge of filtration.

EXAMPLES

The following examples are given to illustrate this invention without limiting the scope thereof, which scope is determined by this entire specification including the appended claims.

All measurements were performed in a double beam Perkin-Elmer Lamda 9 spectrophotometer using matched cells of 1 mm pathlength. Since measurements were made in the near infrared wavelengths, cells of Intrasil quartz were utilized.

EXAMPLES 1-4

This example is given to illustrate the absorbency behavior of four raw commercial resids on dilution with up to 70 wt % of a virgin distillate cutter stock. In all cases the absorbency decreases monotonically with increase of cutter stock, as would be expected in the absence of incompatible sediment. The results are shown in Table I. Examples 1-4 are not within the scope of the present invention.

TABLE I

ABSORBENCY OF RAW RESID BLENDS

| Example | Resid | Blend, Wt % Resid | Blend, Wt % Cutter | Sediment (M1006 nm) | Absorbency (@ 1600 nm) |
| --- | --- | --- | --- | --- | --- |
| 1. | A | 50.0 | 50.0 | tr | 0.36 |
| | A | 40.0 | 60.0 | tr | 0.30 |
| | A | 30.0 | 70.0 | tr | 0.26 |
| 2. | B | 50.0 | 50.0 | tr | 0.44 |
| | B | 40.0 | 60.0 | tr | 0.35 |
| | B | 30.0 | 70.0 | tr | 0.28 |
| 3. | C | 50.0 | 50.0 | tr | 0.68 |
| | C | 40.0 | 60.0 | tr | 0.61 |
| | C | 30.0 | 70.0 | tr | 0.40 |
| 4. | D | 50.0 | 50.0 | tr | 0.74 |
| | D | 40.0 | 60.0 | tr | 0.62 |
| | D | 30.0 | 70.0 | tr | 0.43 |

Notes:
A = Torrance VTB (Vacuum Tower Bottoms)
B = Hondo VTB
C = Arab Heavy VTB
D = Joliet VTB

EXAMPLES 5-7

In these examples, samples of Arab Light VTB (Vacuum Tower Bottoms) visbroken at 400, 600 and 800 ERT were blended with increasing amounts of cutter stock, and the sediment (M1006) and absorbency of each blend measured.

The visbroken resids were first blended to about 180 cs (85 wt % resid, 15 wt % cutter) with either light cycle oil (5%–95% boiling range 357°–673° F.) or heavy cycle oil (5%–95% boiling range 623°–816° F.) from Arab Light, and then further blended with virgin distillate cutter stock of about the same boiling range.

TABLE II

ABSORBENCY OF ARAB LIGHT VTB

| Example | Severity (ERT) | Notes | Blend, Wt % Resid | Blend, Wt % Cutter | Sediment (M1006) | Absorbency (@ 1660 nm) |
| --- | --- | --- | --- | --- | --- | --- |
| 5. | 400 | A | 60.5 | 39.5 | tr | 0.50 |
| | 400 | B | 55.7 | 44.3 | tr | 0.50 |
| | 400 | A | 49.6 | 50.5 | tr | 0.46 |
| | 400 | B | 49.6 | 50.5 | tr | 0.45 |
| | 400 | A | 38.9 | 61.1 | tr | 0.37 |
| | 400 | B | 38.9 | 61.1 | tr | 0.36 |
| 6. | 600 | A | 62.0 | 38.0 | tr | 0.50 |
| | 600 | B | 56.9 | 43.1 | tr | 0.50 |

TABLE II-continued
ABSORBENCY OF ARAB LIGHT VTB

| Example | Severity (ERT) | Notes | Blend, Wt % Resid | Blend, Wt % Cutter | Sediment (M1006) | Absorbency (@ 1660 nm) |
|---|---|---|---|---|---|---|
| | 600 | A | 53.1 | 46.9 | tr | 0.54 |
| | 600 | B | 53.1 | 46.9 | tr | 0.56 |
| | 600 | A | 42.5 | 57.5 | tr | 0.45 |
| | 600 | B | 42.5 | 57.5 | tr | 0.53 |
| | 600 | A | 31.8 | 68.2 | tr | 0.38 |
| | 600 | B | 31.8 | 68.2 | tr | 0.38 |
| | 600 | A | 21.3 | 83.0 | 0.65 | 1.00 |
| | 600 | B | 21.3 | 83.0 | 0.65 | 0.95 |
| 7. | 800 | A | 63.4 | 36.6 | tr | 0.70 |
| | 800 | B | 58.1 | 42.0 | 0.15 | 1.50 |
| | 800 | A | 53.1 | 46.9 | 0.25 | 1.00 |
| | 800 | B | 53.1 | 46.9 | 0.65 | 1.90 |
| | 800 | A | 42.5 | 57.5 | 1.00 | 1.80 |
| | 800 | B | 42.5 | 57.5 | 1.40 | 2.30 |

Notes:
A: to 180 cs with Arab Light Light Cycle Oil
B: to 180 cs with Arab Light Heavy Cycle Oil

EXAMPLES 8-9

These examples illustrate the absorbency of Arab Heavy VTB visbroken at 424 and 605 ERT and diluted with increasing amounts of distillate cutter stock. No incompatible blends are found over the dilution range shown.

TABLE III
ABSORBENCY OF ARAB HEAVY VTB

| Example | Severity (ERT) | Blend, Wt % Resid | Blend, Wt % Cutter | Sediment (M1006) | Absorbency (@ 1600 nm) |
|---|---|---|---|---|---|
| 8. | 424 | 64.2 | 35.8 | tr | 0.67 |
| | 424 | 47.3 | 52.7 | tr | 0.76 |
| | 424 | 47.0 | 53.0 | tr | 0.73 |
| | 424 | 45.5 | 54.5 | tr | 0.59 |
| | 424 | 42.5 | 57.5 | tr | 0.65 |
| | 424 | 42.5 | 57.5 | tr | 0.69 |
| | 424 | 38.7 | 61.3 | tr | 0.78 |
| | 424 | 38.4 | 61.6 | tr | 0.67 |
| 9. | 605 | 66.5 | 33.5 | tr | 0.79 |
| | 605 | 49.7 | 50.3 | tr | 0.87 |
| | 605 | 49.3 | 50.7 | tr | 0.84 |
| | 605 | 49.2 | 50.8 | tr | 0.67 |

EXAMPLES 10-11

In these examples the vacuum tower bottoms from a blend of 50:50 Arab Light and Shengli visbroken to 725 and to 915 ERT were blended with cutter stock. The behavior is summarized in Table IV.

TABLE IV
ABSORBENCY OF 50% ARAB LT/50% SHENGLI

| Example | Severity (ERT) | Blend, Wt % Resid | Blend, Wt % Cutter | Sediment (M1006) | Absorbency (@ 1600 nm) |
|---|---|---|---|---|---|
| 10. | 725 | 62.6 | 37.4 | tr | 0.76 |
| | 725 | 61.4 | 38.6 | tr | 0.76 |
| | 725 | 56.2 | 43.8 | tr | 0.69 |
| | 725 | 55.6 | 44.4 | tr | 0.68 |
| 11. | 915 | 66.0 | 34.0 | 0.9 | 0.99 |
| | 915 | 64.9 | 35.1 | 2.4 | 1.36 |
| | 915 | 59.3 | 40.7 | 0.8 | 0.98 |

What is claimed is:

1. A method for controlling the severity of visbreaking, which method comprises:

sampling the effluent from a visbreaker;

preparing three blends of said effluent with a distillate cutter stock, the first at a viscosity higher than that of a specific viscosity for the visbroken product, the second at a viscosity about equal to the specific viscosity, and the third at a viscosity lower than the specific viscosity;

measuring the total light absorbance of each of said blends at a selected wavelength in the range of 1200 to 3000 nm to determine the presence or absence of incompatible sediment by the total light absorbance of said samples at the selected wavelength;

and adjusting visbreaker severity as needed to maintain compatibility in said first and second samples as evidenced by the absence of incompatible sediment in said first and second samples and to force incompatibility on said third sample as evidenced by the formation during the visbreaking of incompatible sediment.

2. The method described in claim 1 wherein said first blend has a viscosity of 40 cs, said second blend a viscosity of about 30 cs, and said third blend a viscosity of 20 cs.

3. The method described in claim 1 wherein said first blend has a viscosity of 40 cs, said second blend a viscosity of about 30 cs, and said third blend a viscosity of 20 cs.

4. The method described in claim 1 wherein said absorption measurement is made at a temperature of about 150° F. to about 250° F.

5. The method described in claim 1 wherein the slope of a curve representing the total light absorbance of said samples is determined, a negative slope from the absorbance of said first sample to said third sample being indicative of absence of existent incompatible sediment in said third sample and a positive slope from the absorbance of said first sample to the absorbance of said third sample being indicative of the presence of existent incompatible sediment in said third sample.

* * * * *